United States Patent [19]

Cognioń

[11] 4,044,011
[45] Aug. 23, 1977

[54] PROCESS FOR THE PREPARATION OF 8-HYDROXYQUINOLINE

[75] Inventor: Jean-Marié Cognioń, Saint Genis Laval, France

[73] Assignee: Produits Chimiques Ugine Kuhlmann, Paris, France

[21] Appl. No.: 621,024

[22] Filed: Oct. 9, 1975

[30] Foreign Application Priority Data

Oct. 14, 1974  France .................................. 74.34398

[51] Int. Cl.$^2$ ............................................ C07D 215/24
[52] U.S. Cl. ......................... 260/289 XA; 260/283 SY
[58] Field of Search ................... 260/289 XA, 283 SY

[56] References Cited

FOREIGN PATENT DOCUMENTS

| 977,687 | 11/1950 | France | 260/289 XA |
| 45-16948 | 6/1970 | Japan | 260/289 XA |
| 48-12745 | 4/1973 | Japan | 260/289 XA |

Primary Examiner—Donald G. Daus
Assistant Examiner—D. B. Springer
Attorney, Agent, or Firm—Pennie & Edmonds

[57] ABSTRACT

Substantially increased yields of pure-grade 8-hydroxyquinoline are obtained by gradual addition of a solution of o-nitrophenol in acrolein or in an allylidene acetal or diester, to an aqueous acid solution of o-aminophenol. 8-hydroxyquinoline is an article of commerce having known uses.

14 Claims, No Drawings

PROCESS FOR THE PREPARATION OF 8-HYDROXYQUINOLINE

BACKGROUND OF THE INVENTION

1. Field of the Invention

This invention relates to the preparation of 8-hydroxy-quinoline by reacting o-aminophenol with acrolein or an acrolein derivative in the presence of an oxidizing agent.

2. Description of the Prior Art

French Patent 977,687 describes a variation of Skraup's reaction for preparing quinoline compounds. In particular, a process for preparing 8-hydroxyquinoline is disclosed in which o-aminophenol is reacted with acrolein in the presence of a mineral acid and an oxidizing agent such as o-nitrophenol, the acrolein being introduced preferably as a vapor which may be diluted with nitrogen. The yields are of the order of 60%.

In a process for producing 8-hydroxyquinoline described in Japanese Pat. No. 16,948/70, published Aug. 11, 1970, o-aminophenol is reacted with an acrolein derivative, such as allylidene diacetate, in the presence of a mineral acid and an oxidizing agent. When o-nitrophenol is employed as the oxidizing agent, the conversion of the phenols to 8-hydroxyquinoline is about 60%.

Japanese Patent No. 12,745/73, published Apr. 23, 1973, discloses the synthesis of 8-hydroxyquinoline by introducing acrolein into a mixture of o-aminophenol and o-nitrophenol, the o-nitrophenol being an oxidizing agent, in the presence of a mineral acid and a small quantity of an organic acid having a low molecular weight. The addition of the organic acid to the reaction medium retards the decomposition of the acrolein, and the product obtained is purer. The molar conversion of the total phenols into 8-hydroxyquinoline does not exceed 70%.

SUMMARY OF THE INVENTION

The present applicant has developed a process for producing 8-hydroxyquinoline by reacting o-aminophenol and o-nitrophenol with acrolein or an acrolein derivative which avoids premature decomposition of the reactants and consequently produces high yields of a very pure product. This process comprises gradually introducing 0-nitrophenol in a solution of acrolein or of an acrolein derivative, into an aqueous acid solution of o-aminophenol in a mineral acid or a mixture of a mineral acid and an organic acid. More specifically, the process comprises:

a. forming a first solution of o-nitrophenol in acrolein or an acrolein derivative having the formula

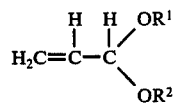
(I)

wherein R[1] and R[2] are the same of different lower alkyl or lower alkyl acyl group containing 1–3 carbon atoms;

b. forming a second solution of o-aminophenol in an aqueous solution of a mineral acid or mixture of a mineral acid and an organic acid;

c. gradually adding the solution from in step (a) to the solution from step (b), thereby causing the mixture to react to form 8-hydroxyquinoline; and d. separating the 8-hydroxyquinoline from the reaction mixture.

The molar conversion of the phenols, o-aminophenol plus o-nitrophenol, to 8-hydroxyquinoline can be as high as 80%.

DESCRIPTION OF THE PREFERRED EMBODIMENTS

According to the process of this invention, when acrolein is used as a solvent for o-nitrophenol, the synthesis of the 8-hydroxyquinoline takes place according to the following overall reaction:

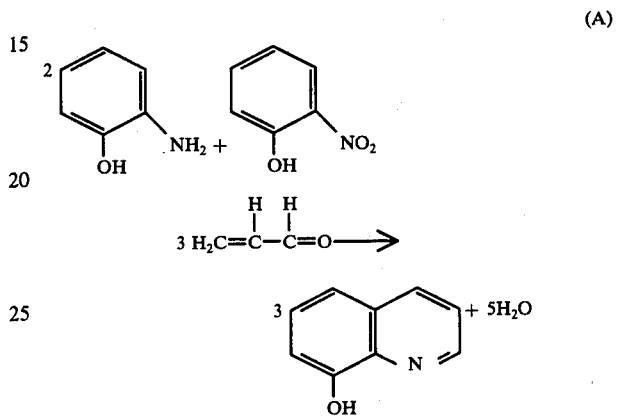

(A)

When a derivative of acrolein is used, a product or products other than water will be produced. Thus, if allylidene diacetate is used, the overall reaction will be:

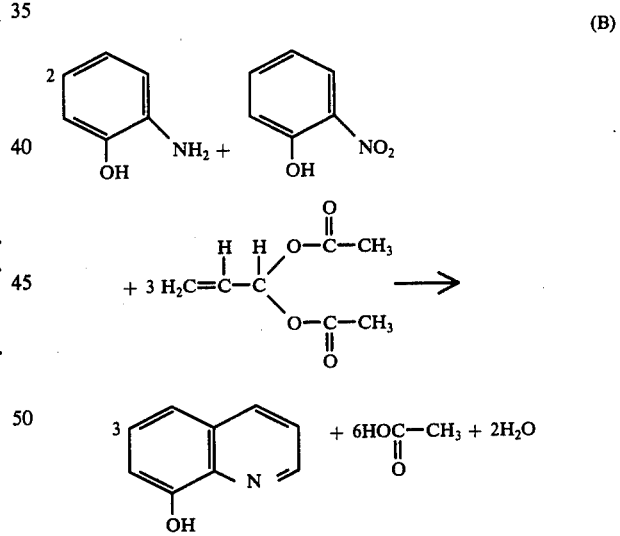

(B)

Acrolein or a derivative of acrolein can be reacted with o-aminophenol to form 8-hydroxyquinoline in the presence of several known oxidizing agents. However, when o-nitrophenol is used as an oxidizing agent, the o-nitrophenol not only acts as an oxidizing agent but also participates in the production of 8-hydroxyquinoline after its reduction to o-aminophenol. Thus, higher yields of 8-hydroxyquinoline compared to the quantity of starting o-aminophenol are obtained when o-nitrophenol is employed as the oxidizing agent.

If acrolein is used to dissolve o-nitrophenol, the acrolein must be sufficiently pure so as not to restrict to any significant extent the rate of conversion or yield of 8-hydroxyquinoline. In particular, it should contain less than about 1.5% of acetaldehyde since the presence of acetaldehyde in a larger quantity would restrict the rate of conversion. Similarly, other acrolein derivatives employed should also be free of impurities to the extent that they will not significantly restrict the rate of conversion or yield of 8-hydroxyquinoline.

The derivatives of acrolein which can be used to dissolve o-nitrophenol are the allylidene diacetals and diesters in which o-nitrophenol will dissolve. Allylidene diacetals and diesters having up to about 3 carbon atoms and which are liquid under the reaction conditions can be used in the process of this invention. In actual practice it would be advantageous to use allylidene diacetals and diesters having the formula

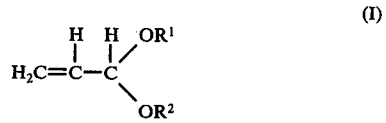

(I)

wherein $R^1$ and $R^2$ are the same or different lower alkyl or lower alkyl acyl group containing 1-3 carbon atoms. Allylidene diacetate, a compound of formula I in which $R^1$ and $R^2$ are each an acetyl group, is the preferred derivative. Allylidene diacetate can exemplarily be prepared by the addition of acrolein to acetic anhydride using a well known technique such as is described at pages 141-142 of C. N. Smith's *Acrolein* (J. Wiley and Sons, London 1962).

The solution of o-nitrophenol and acrolein or a derivative of acrolein can contain variable moles of o-nitrophenol per mole of acrolein or said derivative. The ratio can be varied depending upon the temperature at which the solution is formed and the particular derivative used. Advantageously the solution of o-nitrophenol is at a concentration of about 0.2 to 0.5 moles of o-nitrophenol per mole of acrolein or acrolein derivative.

Any suitable mineral acid can be used in the method of this invention, strong acids such as hydrochloric acid, sulfuric acid, and phosphoric acid being preferred. While the acids are effective over a wide range of concentrations, it is advantageous to use readily available concentrated solutions such as, for example, an aqueous 38% solution of hydrochloric acid.

Organic acids useful in the present invention include the lower aliphatic monocarboxylic acids, such as are disclosed in Japanese Pat. No. 12,745/73. Acetic acid and propionic acid are advantageously employed. The organic acids can be pure or diluted with water. For example, glacial acetic acid is useful, as are more aqueous solutions of acetic acid.

When o-aminophenol is dissolved in an aqueous solution comprising a mineral acid and an organic acid, the solution can advantageously contain from about 0 to 1 mole of organic acid per mole of mineral acid. The acid solution of o-aminophenol can advantageously contain about 0.25 to 1 mole of o-aminophenol per mole of mineral or mixture of mineral acid and organic acid.

The amount of o-aminophenol in solution in a mineral acid or a mixture of a mineral acid and or organic acid to be employed can be varied. It is advantageous to employ the reactants so that the moles of o-aminophenol are approximately twice the moles of o-nitrophenol.

The process of this invention is carried out by first forming a solution of o-nitrophenol in acrolein or an acrolein derivative and then forming a solution of o-aminophenol in an aqueous solution of a mineral acid or a mineral acid and an organic acid. It is desirable to slowly heat the aqueous acid solution of o-aminophenol at, for example, about 90°-120° C., with agitation. The temperature of the reaction mixture can be maintained while the solution of o-nitrophenol in acrolein or an acrolein derivative is then added gradually over a period of one and one-half to two and one-half hours, preferably about two hours.

After the addition of the solution of o-nitrophenol, the reaction mixture can then be heated for a sufficient time to complete the reaction, the time being a period of about fifteen minutes to one and one-half hours, preferably about one hour. Heating at a temperature of about 100°115° C. is preferable. The time and temperature will vary depending upon the reaction mixture and the particular molar ratios of reactants employed.

the 8-hydroxyquinoline can be recovered according to well known procedures. A preferred method of recovery is to subject the reaction mixture to steam distillation for about one hour to distill off any organic acid present and any unconverted o-nitrophenol. A second steam distillation of the reaction mixture after it is rendered alkaline by the addition of a suitable base makes it possible to recover 8- hydroxyquinoline. An aqueous solution of sodium carbonate is useful as a base. Unreacted o-aminophenol remains in solution can be recycled.

The 8-hydroxyquinoline obtained according to this process is a product of high purity which can generally be used for any known application of 8-hydroxyquinoline. For example, 8-hydroxyquinoline is useful in the precipitation, separating and complexing of metals; as a stabilizer of hydrogen peroxide; and as a fungicidal, fungistatic, bactericidal, or bacteristatic agent.

The following examples illustrate the procedure of making 8-hydroxyquinoline according to the present invention in comparison to conventional procedure, and provide evidence of a significant increase in yield obtained for with the new procedure:

EXAMPLE 1 a. In accordance with the processes disclosed in the above-mentioned prior art references, 36.3g (0.33 moles) of o-aminophenol, 24.2g (0.17 moles) of o-nitrophenol, and 100g of an aqueous solution of hydrochloric acid of sp.gr. 1.18 (1 mole) were introduced into a 250-ml pyrex reactor heated by an oil bath and equipped with a reflux condenser, an agitator, and a reagent inlet. When the temperature reached 104°-105° C., 34g (0.60 moles) of acrolein of a purity of 98.5-99% were introduced by means of a proportionating pump during a period of 2 hours, and then the temperature was maintained at 105°-110° C. for 1 hour. After a first steam distillation of the reaction product, 7g (0.05 moles) of unconverted o-nitrophenol were recovered. The subsequent addition of 100 ml of an aqueous solution of sodium hydrocide of sp. gr. 1.33 (1 mole) resulted in the precipitation of the 8-hydroxyquinoline formed, which was then steam-distilled. 30g (0.21 moles) of 8-hydroxyquinoline were collected, which corresponded to a 42% molar conversion of the phenols into 8-hydroxyquinoline. The unconverted o-aminophenol (2g, or 0.02 moles) remained in the reactor.

b. In accordance with the process of this invention, 36.3g (0.33 moles) of o-aminophenol and 100g of an aqueous hydrochloric acid solution of sp. gr. 1.18 (1 mole) were introduced into the reactor described above. A solution of 24.2g (0.17 moles) of o-nitrophenol in 34g (0.60 moles) of acrolein of a purity of 98.5-99% was introduced at 104°-105° C. over a period of 2 hours, and the temperature was maintained at 105°-110° C. for 1 hour. The product was steam distilled and treated as above, and 5g (0.04 moles) of o-nitrophenol, 3g (0.025 moles) of o-aminophenol, and 36g (0.25 moles) of 8-hydroxyquinoline were recovered, which corresponded to a molar conversion of the phenols into 8-hydroxyquinoline of 50%.

EXAMPLE 2 a. In accordance with the processes disclosed in the above-mentioned prior art references, 36.3g (0.33 moles) of o-aminophenol, 24.2g (0.17 moles) of o-nitrophenol, 20g (0.33 moles) of acetic acid, and 100g of a hydrochloric acid solution of sp. gr. 1.18 (1 mole) were introduced into the reactor described in Example 1(a). The temperature was raised to 104°-105° C., and over a period of 2 hours b 34g (0.60 moles) of acrolein of a purity of 98.5-99% were introduced into the reaction mixture. The temperature was then maintained at 105°-110° C. for 1 hour. After a first steam distillation, 4g (0.03 moles) of unconverted o-nitrophenol and 19.7g (0.33 moles) of acetic acid were recovered. The addition of 100 ml of an aqueous solution of sodium hydroxide of sp. gr. 1.33 (1 mole) resulted in the precipitation of 49g (0.34 mole) 8-hydroxyquinoline, which was extracted by a second steam distillation. The unconverted o-aminophenol (1g, or 0.01 moles) remained in aqueous solution in the reactor. The molar conversion of the phenols into 8-hydroxyquinoline was 68%.

b. In accordance with the process of this invention, 36.3g (0.33 moles) of o-aminophenol, 20g (0.33 moles) of acetic acid, and 100g of a hydrochloric acid solution of a sp. gr. of 1.18 (1 mole) were introduced into the reactor described in Example 1(a). At 104°-105° C. a solution of 24.2g (0.17 moles) of o-nitrophenol in 34g (0.60 moles) of acrolein of a purity of 98.5-99% was introduced over a period of 2 hours, and then the mixture was maintained at 105-110° C. for 1 hour. The product was subjected to the steam distillation treatment described in Example 1(a), and 5g (0.04 moles) of o-nitrophenol, 20g (0.33 moles) of accetic acid, 2g (0.02 moles) of o-aminophenol, and 58g (0.4 moles) of 8-hydroxyquinoline were recovered. The molar conversion of the phenols into 8-hydroxyquinoline was 80%.

EXAMPLE 3 a. In accordance with the process disclosed in the above-mentioned prior art references, 336.3 (0.33 moles) of o-aminophenol, 24.2g (0.17 moles) of o-nitrophenol, and 100g of a hydrochloric acid solution of sp. gr. 1,18 (1 mole) were introduced into the reactor described in Example 1(a). Over a period of 2 hours 79g (0.5 moles) of allylidene diacetate were introduced at 104°-105° C., and then the temperature was maintained at 105°-110° C. for one hour. A first steam distillation resulted in recovery of 1g (0.01 moles) of unconverted o-nitrophenol and the acetic acid resulting from the decomposition of the allylidene diacetate. 100 ml of an aqueous solution of sodium hydroicide of sp. gr. 1.33 (1 mole) were added, which caused the precipitation off 50g (0.35 moles) of 8-hydroxyquinoline. The 8-hydroxyquinoline wasextracted by a second steam distillation. The unconverted o-aminophenol (1g, 0.01 moles) remained in aqueous solution in the reactor. The molar conversion of the phenols into 8-hydroxyquinoline was 70%.

b. According to the process of this invention, 36.3g (0.33 moles) of o-aminophenol and 100g of a hydrochloric acid solution of sp. gr. 1.18 (1 mole) were introduced into the reactor described in Example 1(a). The reactor was heated at 104°-105° C., and over a period of 2 hours a solution of 24.2g (0.17 moles) of o-nitrophenol in 79g (0.5 moles) of allylidene diacetate was introduced. The temperature was maintained at 105-110° C. for 1 hour. The reaction product was subjeted to the treatment described in Example 1(a), and 1g (0.01 mole) of o-nitrophenol, 2g (0.02 moles) of aminophenol, and 58g (0.4 moles) of 8-hydroxyquinoline were recovered. The molar conversion of the phenols into 8-hydroxyquinoline was 80%.

In each of these examples, there is described in parallel the processing of identical amounts of the same reactants by a conventional procedure and by the procedure of the present invention, respectively. In Example 1(a), o-aminophenol, o-nitrophenol, and hydrochloric acid solution were first all mixed together and then acrolein was added gradually over a period of two hours, followed by one hour of additional heating. The yield was 42%. On the other hand, in Example 1(b), only o-aminophenol was first dissolved in the hydrochloric acid solution, and o-nitrophenol in solution in acrolein was added gradually over a period of time followed by additional heating. The yield was 50%.

In Example 2(a), o-aminophenol, o-nitrophenol, acetic acid and a hydrochloric acid solution were first all mixed together and then acrolein was added gradually over a period of two hours, followed by one hour of additional heating. The yield was 68%. In Example 2(b), only o-aminophenol was first dissolved in the acetic acid and hydrochloric acid solution, and o-nitrophenol in solution in acrolein was added gradually over a period of time followed by additional heating. The yield was 80%.

In Example 3(a), o-aminophenol, o-nitrophenol, and a hydrochloric acid solution were first all mixed together and then allylidene diacetate was added gradually over a period of two hours, followed by one hour of additional heating. The yield was 70%. In Example 3(b), only o-aminophenol was first dissolved in the hydrochloric acid solution, and o-nitrophenol in solution in allylidene diacetate was added gradually over a period of time followed by additional heating. The yield was 80%.

In summary, in each example it was found that the method of the instant invention achieved an increase of more than 10% in the yield of pure 8-hydroxyquinoline based on the total moles of the two starting phenols.

I claim:

1. In a process for the preparation of 8-hydroxyquinoline by reacting o-aminophenol, o-nitrophenol, and acrolein or an allylidene diacetal or diester, the improvement which comprises the steps of:
   a. forming a first solution of o-nitrophenol in acrolein or an acrolein derivative having the formula

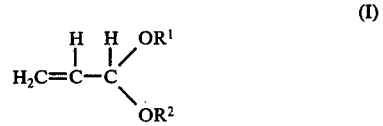

(I)

wherein $R^1$ and $R^2$ are the same or different lower alkyl or lower alkanoyl group of 1–3 carbon atoms;
  b. forming a second solution of o-aminophenol in an aqueous solution of a mineral acid selected from the group of hydrochloric acid, phosphoric acid and sulfuric acid or a mixture of said mineral acid and a lower mono-alkanoic acid;
  c. gradually adding the solution from step (a) to the solution from (b), at a temperature of from about 90° to 120° C thereby causing the mixture to react to form 8-hydroxyquinoline; and
  d. separating the 8-hydroxyquinoline from the reaction mixture.

2. A process in accordance with claim 1 wherein the solution of o-nitrophenol contains from about 0.20 to 0.50 moles of o-nitrophenol to one mole of acrolein or an acrolein derivative.

3. A process in accordance with claim 1 wherein the mineral acid is hydrochloric acid.

4. A process in accordance with claim 1 wherein a lower mono-alkanoic acid is present and the lower mono-alkanoic acid is acetic acid.

5. A process in accordance with claim 4 wherein the solution of o-nitrophenol contains from about 0.20 to 0.50 moles of o-nitrophenol to one mole of acrolein or an acrolein derivative.

6. A process in accordance with claim 1 wherein the acrolein derivative is allylidene diacetate.

7. A process in accordance with claim 6 wherein the lower mono-alkanoic acid is present and the lower mono-alkanoic acid is acetic acid.

8. A process in accordance with claim 6 where in the solution of o-nitrophenol contains from 0.20 to 0.50 moles of o-nitrophenol to one mole of allylidene diacetate.

9. A process in accordance with claim 6 wherein the mineral acid is hydrochloric acid.

10. A process in accordance with claim 6 wherein the mixture of said mineral acid and a lower mono-alkanoic acid is a mixture of hydrochloric acid and acetic acid.

11. A process in accordance with claim 10 wherein the acid mixture contains from 0 to 1 mole of acetic acid for one mole of hydrochloric acid.

12. A process in accordance with claim 1 wherein the mixture of said mineral acid and a lower mono-alkanoic acid is a mixture of hydrochloric acid and acetic acid.

13. A process in accordance with claim 12 wherein the acid mixture contains from 0 to 1 mole of acetic acid for one mole of hydrochloric acid.

14. A process in accordance with claim 13 wherein the solution of o-nitrophenol contains from about 0.20 to 0.50 moles of o-nitrophenol to one mole of acrolein or an acrolein derivative.

* * * * *

UNITED STATES PATENT AND TRADEMARK OFFICE
CERTIFICATE OF CORRECTION

PATENT NO. : 4,044,011
DATED : August 23, 1977
INVENTOR(S) : Jean-Marie Cognion

It is certified that error appears in the above-identified patent and that said Letters Patent are hereby corrected as shown below:

Column 3, Line 50, reads "more acqueous", should read --more dilute acqueous--

Column 5, Line 52, reads "336.3", should read --36.3--

Column 6, Line 13, reads "of aminophenol", should read --of o-aminophenol--

Signed and Sealed this

Twenty-fourth Day of January 1978

[SEAL]

Attest:

RUTH C. MASON
Attesting Officer

LUTRELLE F. PARKER
Acting Commissioner of Patents and Trademarks